United States Patent [19]
Mondet et al.

[11] Patent Number: 6,113,930
[45] Date of Patent: *Sep. 5, 2000

[54] COSMETIC COMPOSITION COMPRISING A FILM-FORMING POLYMER, PREPARATION, AND USE THEREOF

[75] Inventors: Jean Mondet, Aulnay Sous Bois; Roland Ramin, Itteville, both of France

[73] Assignee: L'Oreal, France

[ * ] Notice: This patent is subject to a terminal disclaimer.

[21] Appl. No.: 09/165,313

[22] Filed: Oct. 2, 1998

Related U.S. Application Data

[63] Continuation of application No. 08/672,090, Jun. 27, 1996, Pat. No. 5,817,304.

[30] Foreign Application Priority Data

Jun. 27, 1995 [FR] France .................................. 95 07732

[51] Int. Cl.⁷ .................................................. A61K 7/043
[52] U.S. Cl. ........................ 424/401; 424/61; 424/78.03; 514/937
[58] Field of Search ........................ 424/401, 61, 78.03; 514/937

[56] References Cited

U.S. PATENT DOCUMENTS

| | | | |
|---|---|---|---|
| 4,158,053 | 6/1979 | Greene et al. | 424/61 |
| 4,301,046 | 11/1981 | Schlossman | 523/105 |
| 4,384,058 | 5/1983 | Galante | 524/32 |
| 4,421,881 | 12/1983 | Benkendorf et al. | 524/24 |
| 4,818,589 | 4/1989 | Johnson et al. | 428/201 |
| 5,057,312 | 10/1991 | Langla et al. | 424/61 |
| 5,587,145 | 12/1996 | Lion et al. | 424/45 |
| 5,603,939 | 2/1997 | Ser | 424/401 |
| 5,607,665 | 3/1997 | Calello et al. | 424/61 |
| 5,612,107 | 3/1997 | Sangani et al. | 428/41.7 |
| 5,639,447 | 6/1997 | Patel | 424/61 |
| 5,645,823 | 7/1997 | Thrall et al. | 424/61 |
| 5,662,891 | 9/1997 | Martin | 424/61 |
| 5,667,768 | 9/1997 | Ramin | 424/61 |
| 5,670,141 | 9/1997 | Nehra | 424/61 |
| 5,672,647 | 9/1997 | Poterie et al. | 524/463 |
| 5,683,681 | 11/1997 | Ramin et al. | 424/61 |
| 5,720,804 | 2/1998 | Martin | 106/170.2 |
| 5,720,943 | 2/1998 | Mougin et al. | 424/61 |
| 5,817,304 | 10/1998 | Mondet et al. | 424/78.03 |
| 5,830,440 | 11/1998 | Sturla et al. | |
| 5,961,989 | 10/1999 | Mougin et al. | 424/401 |
| 6,001,338 | 12/1999 | Mondet | 424/61 |

FOREIGN PATENT DOCUMENTS

| | | |
|---|---|---|
| 0 291 555 | 11/1988 | European Pat. Off. . |
| 418469 | 3/1991 | European Pat. Off. . |
| 0 628 304 | 12/1994 | European Pat. Off. . |
| 644750 | 4/1996 | European Pat. Off. . |
| 04103514 | 4/1992 | Japan . |
| 04103515 | 4/1992 | Japan . |
| 5-148122 | 6/1993 | Japan . |
| 5-155737 | 6/1993 | Japan . |
| 6-21049 | 3/1994 | Japan . |
| 6-504792 | 6/1994 | Japan . |
| WO 91/15187 | 10/1991 | WIPO . |

OTHER PUBLICATIONS

Patent Abstracts of Japan for JP04103514.
Patent Abstracts of Japan for JP04103515.
The Penguin Dictionary of Chemistry, p. 72, 1985.
The Penguin Dictionary of Chemistry, p. 130, 1985.
The Penguin Dictionary of Chemistry, p. 168, 1985.
The Merck Index, p. 545, 1976.
Derwent abstract for JP4103514.
Derwent abstract for JP4103515.
Derwent abstract for EP0628304.
CRC Handbook of Chemistry and Physics, $1^{st}$ Student Ed., p. C–245, 1988.
Technical Leaflet, Worléesol.
Technical Leaflet, Worléesol 60 (with translation).
Material Safety Data Sheet for RHOPLEX–R WL–81 Emulsion, Apr. 12, 1991.
Rhome and Haas, RHOPLEX WL For Acrylic Lacquers Formulation Guide, Dec. 1987.
Partial Translation of Japanese Patent Application Kokai 4–103514.
Partial Translation of Japanese Patent Application Kokai 4–103515.
Partial Translation of Japanese Patent Publication 6–21049.

Primary Examiner—Robert H. Harrison
Attorney, Agent, or Firm—Finnegan, Henderson, Farabow, Garrett & Dunner

[57] ABSTRACT

The present invention is directed to a cosmetic composition comprising at least one neutralized ionic film-forming polymer, water and least one polar organic solvent which is at least partially water-miscible and of higher boiling point than the boiling point of water, wherein the film-forming polymer is insoluble in water and is soluble in the organic solvent when it is in a non-neutralized state. In addition the neutralized film-forming polymer is soluble in the mixture of organic solvent and water and further wherein the mixture of neutralized polymer, organic solvent and water is a single phase, where the single phase is a homogeneous solution.

47 Claims, No Drawings

COSMETIC COMPOSITION COMPRISING A FILM-FORMING POLYMER, PREPARATION, AND USE THEREOF

This is a continuation of application of U.S. application Ser. No. 08/672,090, filed Jun. 27, 1996, now U.S. Pat. No. 5,817,304 which is incorporated herein by reference.

The present invention relates to a cosmetic composition comprising a film-forming polymer, water and at least one polar organic solvent which is at least partially water-miscible.

It is common practice in many cosmetic formulations to use a variable proportion, depending on the nature of the formulation, of at least one film-forming substance which makes it possible, for example in the context of a hair composition, to impart more hold and softness to the hair, or, in the context of a nail varnish, to impart a hard and shiny film which adheres perfectly to the nails. The film-forming substance should, however, have a good affinity towards nail and hair keratin.

In other words, once the composition had been applied, the film-forming substance should display remanence properties, that is to say properties of being difficult to remove from its support by simple washing with water or with the aid of a shampoo.

It is known in the state of the art to use compositions in which the film-forming substance is in a solvent medium. However, since the use of volatile organic solvents is harmful to the environment and to keratin substances, it is thus sought to reduce the content of volatile organic solvents in cosmetic compositions, or to omit them altogether.

In order to compensate for the omission of the organic solvents in film-forming compositions, it is known to use aqueous dispersions of polymers (latex or pseudolatex) as film-forming substance, in which the polymer, which is water-insoluble, is dispersed in the form of particles. With the polymer being in particulate form, its filmification is achieved by coalescence of the particles at a speed which depends, in particular, on the intrinsic properties of the polymer.

In order for the filmification between the particles to occur rapidly at room temperature, so as to obtain correct mechanical properties for the deposited film, it is preferable for the glass transition temperature of the polymer to be low and in the region of 0° C. However, if it is desired for the film to have a correct hardness, in particular for a use in a nail varnish, it is preferable for the polymer to have a glass transition temperature in the region of 30° C.

It is difficult to obtain a film-forming composition which forms a film rapidly at room temperature and gives a film which is of good hardness after drying, even by using a mixture of several aqueous dispersions. Moreover, the addition of plasticizers and/or coalescence agents does not always make it possible to achieve the best properties desired.

Film-forming compositions comprising a polymer in a mixture of water and organic solvent are also known.

Application WO 91/15187, describes a hair shaping composition in the form of an emulsion in which a mixture of polymer and organic solvent is dispersed in an aqueous phase.

Application JP 63-28411, describes a nail varnish composition based on resin, organic solvent, water and a water-miscible compound. The composition is in the form of a water-in-oil emulsion, the oily phase comprising the organic solvent and the resin, the aqueous phase comprising the water and the water-miscible compound.

These compositions in emulsion form do not dry rapidly, are not applied easily to the nail, and the film obtained after drying does not have excellent staying power.

The aim of the present invention is to provide a film-forming composition which is of rapid filmification while at the same time retaining good film-forming properties, in particular giving a film which is of good hardness.

Thus, the subject of the present invention is a cosmetic composition comprising at least one neutralized ionic film-forming polymer, water and at least one polar organic solvent which is at least partially water-miscible and higher in boiling point than the boiling point of water, the film-forming polymer being insoluble in water and soluble in the organic solvent when it is in the non-neutralized state, and being soluble in the mixture of organic solvent and water when it is neutralized, the mixture of the neutralized polymer, the organic solvent and water constituting a single phase.

The subject of the present invention is also a process for the preparation of a cosmetic composition, in which a non-neutralized ionic film-forming polymer, which is water-insoluble in the non-neutralized state, is dissolved in a polar organic solvent which is at least partially water-miscible and of higher boiling point than the boiling point of water, the polymer being soluble in a mixture of water and the organic solvent when it is neutralized, followed by addition of water to the organic solutions, the water and/or the organic solvent comprising at least one agent for neutralizing the polymer, the mixture of the neutralized polymer, the organic solvent and the water constituting a single phase.

The invention also relates to the use in cosmetics of a composition comprising a neutralized ionic film-forming polymer, water and at least one polar organic solvent which is at least partially water-miscible and of higher boiling point than the boiling point of water, the film-forming polymer being insoluble in water and soluble in the organic solvent when it is in the non-neutralized state, and being soluble in the mixture of organic solvent and water when it is neutralized, the mixture of the neutralized polymer, the organic solvent and the water constituting a single phase.

In the remainder of the present description, the expression "solvent which is at least partially water-miscible" is understood to refer to any solvent whose solubility in water is greater than or equal to 10% by weight, at 25° C.

The expression "water-insoluble polymer" is understood to refer to any polymer whose solubility in water is less than or equal to 2% by weight, at 25° C.

The expression "non-neutralized ionic polymer" is understood to refer to any ionic polymer in which all the ionic functions are free.

The expression "neutralized ionic polymer" is understood to refer to any polymer in which the ionic functions are at least partially neutralized, it being possible for the degree of neutralization to be within the range from 5% to 100%.

The expression "a single phase" is understood to refer to a homogeneous solution. It can also be understood to mean a colloidal suspension of the polymer in the water-solvent mixture.

The composition according to the invention thus comprises at least one neutralized ionic film-forming polymer, water and a polar organic solvent which is at least partially water-miscible and of boiling point higher than the boiling point of water.

The ionic polymer, which is water-insoluble in the non-neutralized state, may preferably have a molecular weight, determined by steric exclusion chromatography, ranging from 500 to 200,000, and more preferably ranging from 1000 to 80,000.

When molecular weight is determined by steric exclusion chromatography, one skilled in the art determines molecular weight by comparing the summit of the peak of the polymer in gaseous phase chromatography with that of the standard peak of polystyrene. Molecular weight determined by this method generally fails between the weight average molecular weight and the number average molecular weight.

The ionic polymer may preferably include at least one hydrophilic part and at least one hydrophobic part in its structure.

The hydrophilic part of the polymer may comprise at least one highly polar group, which interacts strongly with water. Highly polar groups which may be mentioned are the carboxylic acid group and salts thereof, the sulphonic acid group and salts thereof, the phosphonic acid group and salts thereof, primary, secondary or tertiary amine groups and salts thereof, quaternary amine groups, a hydroxyl group, a hydrophilic amide group, an ether or polyether group or a nitrile, amido, nitro, imido or mercapto group.

Preferably, the ionic polymer includes anionic groups chosen from carboxylic acid, sulphonic acid and/or phosphonic acid groups. The monomers bearing such groups may preferably be present in the polymer at a content ranging from 3 to 30% by weight relative to the total weight of the polymer, and more preferably from 5 to 20%. The anionic group is advantageously a carboxylic acid group.

In order to make the polymer compatible with water, that is to say in order to prevent the precipitation of the polymer in the composition, the anionic groups are preferably neutralized with a base to a degree of neutralization ranging from 5 to 100%. A volatile base such as ammonia or triethylamine is preferably used.

When the polymer includes cationic groups, these groups may be preferably neutralized with an acid to a degree of neutralization ranging from 5 to 100%. Acetic acid may be used, for example.

The lipophilic part of the polymer may preferably comprise relatively non-polar groups and/or of hydrophobic groups. These groups may be, for example, a linear or branched, saturated or unsaturated aliphatic hydrocarbon radical, an aromatic hydrocarbon radical, a saturated or unsaturated cyclic hydrocarbon radical, a fluorocarbon radical or an organosilicon radical. The number of carbon atoms in these groups may preferably range approximately from 1 to 30.

The ionic polymer is advantageously chosen from radical polymers, polycondensates and polymers of natural origin.

The radical polymers may preferably be chosen from acrylic polymers and vinyl polymers.

As a monomer bearing an anionic group which may be used during the radical polymerization, mention may be made of acrylic acid, methacrylic acid, crotonic acid, maleic anhydride or 2-acrylamido-2-methylpropanesulphonic acid.

The acrylic polymers may preferably result from the copolymerization of monomers chosen from esters and/or amides of acrylic acid or of methacrylic acid. Examples of monomers of ester type which may be mentioned are methyl methacrylate, ethyl methacrylate, butyl methacrylate, isobutyl methacrylate, 2-ethylhexyl methacrylate and lauryl methacrylate. Examples of monomers of amide type which may be mentioned are N-t-butylacrylamide and N-t-octylacrylamide.

Acrylic polymers obtained by copolymerization of ethylenically unsaturated monomers containing hydrophilic groups, preferably of nonionic nature, such as hydroxyethyl acrylate, 2-hydroxypropyl acrylate, hydroxyethyl methacrylate or 2-hydroxypropyl methacrylate, are preferably used.

The vinyl polymers may preferably result from the homopolymerization or copolymerization of monomers chosen from vinyl esters, styrene or butadiene. Examples of vinyl esters which may be mentioned are vinyl acetate, vinyl neodecanoate, vinyl pivalate, vinyl benzoate and vinyl t-butylbenzoate.

According to the invention, the polycondensates may preferably be chosen from polyesters, polyester amides, fatty-chain polyesters (alkyd resins), and epoxyester resins. The polyesters may be obtained, in a known manner, by polycondensation of aliphatic or aromatic diacids with aliphatic or aromatic diols or polyols. Aliphatic diacids which may be used are succinic acid, glutaric acid, adipic acid, pimelic acid, suberic acid or sebacic acid. Aromatic diacids which may be used are terephthalic acid or isophthalic acid, or alternatively a derivative such as phthalic anhydride. Aliphatic diols which may be used are ethylene glycol, propylene glycol, diethylene glycol, neopentyl glycol, cyclohexanedimethanol or 4,4'-(1-methylpropylidene) bisphenol. Polyols which may be used are glycerol, pentaerythritol, sorbitol or trimethylol propane.

The polyester amides may be obtained in a similar manner to the polyesters, by polycondensation of diacids with diamines or amino alcohols. Diamines which may be used are ethylenediamine, hexamethylenediamine or meta- or para-phenylenediamine. An amino alcohol which may be used is monoethanolamine.

As monomer bearing an anionic group which may preferably be used during the polycondensation, mention may be made, for example, of dimethylolpropionic acid, trimellitic acid or a derivative such as trimellitic anhydride, the sodium salt of pentanediol-3-sulphonic acid or the sodium salt of 5-sulpho-1,3-benzenedicarboxylic acid.

The fatty-chain polyesters may be obtained by the use of fatty-chain diols during the polycondensation.

The epoxyester resins may be obtained by polycondensation of fatty acids with a condensate containing α, ω-diepoxy ends. Such polymers are described in particular in K. Krishnamurti, Progress in Organic Coatings, 11 (1983), 167–197, which is specifically incorporated by reference herein.

Shellac may be mentioned as a polymer of natural origin.

According to the invention, the organic solvent is at least partially water-miscible and has a boiling point higher than that of water. It may be totally water-miscible.

The organic solvent is preferably chosen from propylene glycol, propylene glycol monomethyl ether, ethyl lactate, propylene glycol monopropyl ether, propylene glycol mono-tert-butyl ether and propylene glycol monomethyl ether acetate, alone or as a mixture.

According to the invention, the content of film-forming polymer may preferably range from 10 to 70% by weight relative to the total weight of the composition.

The content of organic solvent which is at least partially water-miscible and of boiling point higher than the boiling point of water may preferably range from 4 to 48% by weight relative to the total weight of the composition.

The water content may preferably range from 12 to 75%, and more preferably from 40 to 70%, by weight relative to the total weight of the composition.

Preferably, the ratio between the water content and the content of organic solvent which is at least partially water-miscible and of boiling point higher than the boiling point of water, in the composition according to the invention, ranges preferably from 0.25:19 and more preferably from 0.8:17.

The composition may additionally comprise at least one second polar organic solvent which is at least partially water-miscible and which has a boiling point below or equal to the boiling point of water.

Such a solvent may be chosen in particular from acetone, methyl ethyl ketone, isopropanol, isobutanol, ethanol, dimethoxyethane and amyl acetate, and mixtures thereof.

The at least one second organic solvent may be present in the composition at a content preferably ranging from 0 to 40% by weight relative to the total weight of the composition.

The at least one second organic solvent makes it possible to facilitate the use and dissolution of the polymer in the organic solvent which is at least partially water-miscible and of boiling point higher than the boiling point of water. Thus, the final organic medium can be more fluid, the composition can be applied more easily and it is possible thereby to reduce the amount of organic solvent of boiling point higher than the boiling point of water, present in the composition.

The composition of the invention may also comprise an aqueous polymer dispersion.

Preferably, the dispersed polymer contains no anionic groups or contains such groups to a degree such that it represents not more than 5% by weight of anionic-group-bearing monomer relative to the total weight of dispersed polymer.

The aqueous polymer dispersion may be a latex or a pseudolatex. The expression pseudolatex denotes a suspension comprising generally spherical particles of a polymer, these particles being obtained by dispersion of the polymer in a suitable aqueous phase. The latex is also a suspension comprising particles of a polymer which are obtained directly by polymerization of one or more monomers in a suitable aqueous phase.

The polymer in aqueous dispersion may be chosen from polyurethanes, acrylic polymers, alkyds, polyesters and polyester amides. The polymer in aqueous dispersion preferably has a glass transition temperature of above or equal to 10° C.

The polymer in aqueous dispersion is advantageously an acrylic polymer such as a copolymer of methyl methacrylate or of styrene, with a methyl, ethyl or 2-ethylhexyl acrylate or methacrylate.

The polymer in aqueous dispersion may be present in the composition according to the invention at a content preferably ranging from 30 to 90% by weight of solids relative to the total weight of the composition, and more preferably from 50 to 80%. When the composition according to the invention comprises such an aqueous polymer dispersion, faster filmification of the said composition can be observed, the composition retaining its mechanical and water-resistant properties. The film obtained can be shinier, more adherent and have good surface hardness. Such a composition is particularly suitable for use as a nail varnish.

The composition according to the invention may contain adjuvants commonly used in cosmetics. Examples of adjuvants which may be mentioned are dyes, pigments, pearlescent agents, lakes, anti-UV agents, thickeners, fragrances, anti-foaming agents, surfactants and bactericidal agents.

One skilled in the art will know how to select this or these optional adjuvants, and/or the amount thereof, such that the advantageous properties of the composition according to the invention are not, or are substantially not, altered by the addition envisaged.

Thus, during the use of the composition according to the invention, it is seen that the organic solvent of boiling point higher than the boiling point of water does not totally evaporate until after evaporation of the water and thus serves as a solvent for the polymer during the final stage of filmification of the composition.

The same properties of sheen and hardness of the film as those obtained with a film-forming composition in solvent medium can be obtained, and total filmification of the composition can be faster than with an aqueous polymer dispersion. In particular, the film obtained after drying can be of good sheen, good adhesion and good staying power.

Good wettability of the nail can be observed when the composition according to the invention is applied to the nail, thereby facilitating the application of the composition.

The composition of the invention may be in the form of a hair composition, for example one having a styling action, or in the form of a make-up composition such as a nail varnish or a mascara, or alternatively in the form of a skin care composition such as a beauty mask or a facial care lotion which exerts skin-tightening effects. It may also be present in the form of a nail care composition.

Examples illustrating the present invention will now be given without, however, limiting it.

EXAMPLE 1

A colourless nail care product base having the following composition was prepared:

| | |
|---|---|
| - Alkyd resin with a solids content (SC) of 75%, in a mixture of butyl glycol and 2-butanol (50/50) sold under the name Worleesol 60 A by the company Worlle | 13 g SC |
| - Acrylic aqueous dispersion with a solids content of 42%, sold under the name Primal WL81K by Rohm and Haas | 13 g SC |
| - Isopropanol | 5.5 g |
| - Propylene glycol monomethyl ether | 8.5 g |
| - Triethylamine | 1.2 g |
| - Additives | 0.5 g |
| - Active agents | 0.5 g |
| - Water | qs 100 a |

The alkyd resin, the isopropanol and the propylene glycol monomethyl ether were mixed together with stirring, followed by addition of the additives and the triethylamine. The water and the active agents were then added. Lastly, the acrylic dispersion was added.

The care base spread easily on the nail and rapidly formed a film. After drying, it gave a hard and resistant film.

This base may be coated with a coloured varnish.

EXAMPLE 2

A nail varnish having the following composition was prepared according to the procedure of Example 1:

| | |
|---|---|
| - Alkyd resin with a solids content of 75%, in a mixture of butyl glyco and 2-butanol (50/50) (Worleesol 60 A from Worlle) | 15 g SC |
| - Acrylic aqueous dispersion with a solids content of 42% (Primal WL81K from Rohm and Haas) | 15 g SC |
| - Isopropanol | 6.5 g |
| - Propylene glycol monoethyl ether | 4.5 g |
| - Propylene glycol monobutyl ether | 8.5 g |
| - Triethylamine | 1.3 g |
| - Rheological agent | 0.5 g |
| - Additives | 0.5 g |
| - Pigments | 0.7 g |
| - Water | qs 100 g |

A varnish which is applied easily to the nail was obtained. After drying, the film obtained was smooth and uniform.

EXAMPLE 3

A nail varnish having the following composition was prepared:

| | |
|---|---|
| - Alkyd resin with a solids content of 75%, in a mixture of butyl glycol and 2-butanol (50/50) (Worleesol 60 A from Worlle) | 30 g SC |
| - Isopropanol | 6.5 g |
| - Triethylamine | 2.6 g |
| - Ethanol | 13 g |
| - Rheological agent | 0.5 g |
| - Additives | 0.5 g |
| - Pigments | 0.7 g |
| - Water | qs 100 g |

A varnish which is applied easily to the nail was obtained. After drying, the film obtained was smooth and uniform.

We claim:

1. A cosmetic composition comprising:
   a) at least one neutralized ionic film-forming polymer;
   b) water;
   c) at least one polar organic solvent which is at least partially water-miscible and of higher boiling point than the boiling point of water; and
   d) an aqueous polymer dispersion;
   wherein the film-forming polymer is insoluble in water and is soluble in the organic solvent when it is in a non-neutralized state,
   wherein said neutralized film-forming polymer is soluble in the mixture of organic solvent and water, and
   wherein the mixture of neutralized polymer, organic solvent and water comprises a single phase, said single phase being a homogenous solution.

2. A cosmetic composition according to claim 1, wherein said neutralized ionic film-forming polymer includes at least one hydrophilic part and at least one hydrophobic part.

3. A cosmetic composition according to claim 2, wherein said at least one hydrophilic part comprises at least one highly polar group, wherein said at least one highly polar group is a carboxylic acid group or a salt thereof, a sulphonic acid group or a salt thereof, a phosphonic acid group or a salt thereof, a primary, secondary or tertiary amine group or a salt thereof, a quaternary amine group, a hydroxyl group, a hydrophilic amide group, an ether group, a polyether group, a nitrile group, an amido group, a nitro group, an imido group, or a mercapto group.

4. A cosmetic composition according to claim 1, wherein said neutralized ionic film-forming polymer includes at least one anionic group, wherein said at least one anionic group is a carboxylic acid group, a sulphonic acid group, or a phosphonic acid group, neutralized to a degree ranging from 5 to 100%.

5. A cosmetic composition according to claim 4, wherein said neutralized ionic film-forming polymer includes from 3 to 30% by weight of monomers bearing at least one anionic group relative to the total weight of the polymer.

6. A cosmetic composition according to claim 5, wherein said neutralized ionic film-forming polymer includes from 5 to 20% by weight of monomers bearing at least one anionic group relative to the total weight of the polymer.

7. A cosmetic composition according to claim 4, wherein said at least one anionic group is a carboxylic acid group.

8. A cosmetic composition according to claim 1, wherein said neutralized ionic film-forming polymer includes at least one cationic group neutralized to a degree ranging from 5 to 100%.

9. A cosmetic composition according to claim 1, wherein said neutralized ionic film-forming polymer includes a lipophilic part comprising at least one group, wherein said at least one group is a linear or branched, saturated or unsaturated, aliphatic hydrocarbon radical, a saturated or unsaturated cyclic hydrocarbon radical, a fluorocarbon radical or an organosilicon radical.

10. A cosmetic composition according to claim 9, wherein said unsaturated cyclic hydrocarbon radicals are aromatic hydrocarbon radicals.

11. A cosmetic composition according to claim 9, wherein said at least one group has from 1 to 30 carbon atoms.

12. A cosmetic composition according to claim 1, wherein said neutralized ionic film-forming polymer is one of radical polymers, polycondensates or polymers of natural origin.

13. A cosmetic composition according to claim 12, wherein said radical polymers are acrylic polymers or vinyl polymers.

14. A cosmetic composition according to claim 13, wherein said acrylic polymers are copolymers containing at least two monomers wherein said monomers are acrylic acid esters, methacrylic acid esters, acrylic acid amides or methacrylic acid amides.

15. A cosmetic composition according to claim 14, wherein said methacrylic acid esters are methyl methacrylate, ethyl methacrylate, butyl methacrylate, isobutyl methacrylate, 2-ethylhexyl methacrylate or lauryl methacrylate and wherein said acrylic acid amides are N-t-butylacrylamide or N-t-octylacrylamide.

16. A cosmetic composition according to claim 13, wherein said acrylic polymers are copolymers containing at least two monomers wherein said monomers are hydroxyethyl acrylate, 2-hydroxypropyl acrylate, hydroxyethyl methacrylate or 2-hydroxypropyl methacrylate.

17. A cosmetic composition according to claim 13, wherein said vinyl polymers are homopolymers of a monomer, wherein said monomer is a vinyl ester, styrene, or butadiene or said vinyl polymers are copolymers of at least two monomers, wherein said at least two monomers are vinyl esters, styrene, and butadiene.

18. A cosmetic composition according to claim 17, wherein said vinyl esters are vinyl acetate, vinyl neodecanoate, vinyl pivalate, vinyl benzoate or vinyl t-butylbenzoate.

19. A cosmetic composition according to claim 12, wherein said polycondensates are polyesters, polyester amides, or epoxyester resins.

20. A cosmetic composition according to claim 19, wherein said polyesters are fatty-chain polyesters.

21. A cosmetic composition according to claim 1, wherein said neutralized ionic film-forming polymer has a molecular weight, determined by steric exclusion chromatography, ranging from 500 to 200,000.

22. A cosmetic composition according to claim 21, wherein said neutralized ionic film-forming polymer has a molecular weight, determined by steric exclusion chromatography, ranging from 1000 to 80,000.

23. A cosmetic composition according to claim 1, wherein said at least one polar organic solvent having a boiling point higher than that of water is propylene glycol, propylene glycol monomethyl ether, ethyl lactate, propylene glycol monopropyl ether, propylene glycol mono-tert-butyl ether or propylene glycol monomethyl ether acetate.

24. A cosmetic composition according to claim 1, wherein said composition has a water content ranging from 12 to 75% by weight relative to the total weight of the composition.

25. A cosmetic composition according to claim 1, wherein said at least one polar organic solvent which is water-miscible and of boiling point higher than the boiling point of water is present in an amount ranging from 4 to 48% by weight relative to the total weight of the composition.

26. A cosmetic composition according to claim 1, wherein said neutralized ionic film-forming polymer is present in an amount ranging from 10 to 70% by weight relative to the total weight of the composition.

27. A cosmetic composition according to claim 1, wherein said composition additionally comprises at least one second polar organic solvent which is at least partially water-miscible and which has a boiling point below or equal to the boiling point of water.

28. A cosmetic composition according to claim 27, wherein said at least one second polar organic solvent which is water-miscible and which has a boiling point below or equal to the boiling point of water is acetone, methyl ethyl ketone, isopropanol, isobutanol, ethanol, dimethoxyethane or amyl acetate.

29. A cosmetic composition according to claim 1, wherein said composition additionally comprises at least one cosmetic adjuvant.

30. A cosmetic composition according to claim 1, wherein said composition is in the form of a hair composition, a make-up composition, a skin care composition or a nail care composition.

31. A process for the preparation of a cosmetic composition, according to claim 1, comprising the steps of:
    dissolving at least one non-neutralized ionic film-forming polymer, which is water-insoluble in the non-neutralized state, in a polar organic solvent which is at least partially water-miscible and of higher boiling point than the boiling point of water; and
    adding water to the organic solution, obtained in said dissolving step, to obtain a mixture of said water and said organic solvent, the water and/or the organic solvent comprising at least one agent in an amount effective to neutralize said ionic film-forming polymer, wherein said neutralized ionic film-forming polymer is soluble in said mixture of said water and said organic solvent and further wherein said mixture of said neutralized ionic film-forming polymer, said organic solvent and said water comprises a single phase, said single phase being a homogenous solution.

32. A process according to claim 31, wherein said non-neutralized ionic film-forming polymer includes at least one anionic group and wherein said at least one agent is a volatile base.

33. A method of cosmetically treating keratin comprising the step of applying to said keratin a cosmetically effective amount of the cosmetic composition of claim 1.

34. A cosmetic composition according to claim 1, wherein said cosmetic composition is a nail varnish.

35. A cosmetic composition according to claim 1, wherein said cosmetic composition is a nail care composition.

36. A cosmetic composition comprising:
    a) at least one neutralized ionic film-forming polymer;
    b) water; and
    c) at least one polar organic solvent which is at least partially water-miscible and of higher boiling point than the boiling point of water;
    wherein the film-forming polymer is insoluble in water and is soluble in the organic solvent when it is in a non-neutralized state,
    wherein said neutralized film-forming polymer is soluble in the mixture of organic solvent and water,
    wherein the mixture of neutralized polymer, organic solvent and water comprises a single phase, said single phase being a homogenous solution, and
    wherein said neutralized ionic film-forming polymer is present in an amount ranging from about 30 to 70 percent by weight relative to the total weight of the composition.

37. A cosmetic composition according to claim 36, wherein said cosmetic composition is a nail varnish.

38. A cosmetic composition according to claim 36, wherein said cosmetic composition is a nail care composition.

39. A cosmetic composition according to claim 36, wherein said neutralized ionic film-forming polymer is present in an amount ranging from 30 to 70 percent by weight relative to the total weight of the composition.

40. A cosmetic composition according to claim 36, wherein said composition additionally comprises an aqueous polymer dispersion.

41. A cosmetic composition according to claim 40, wherein the polymer in said aqueous polymer dispersion includes from 0 to 5% by weight of anionic-group-bearing monomer relative to the total weight of the dispersed polymer.

42. A cosmetic composition according to claim 40, wherein the polymer in said aqueous dispersion is a polyurethane, an acrylic polymer, an alkyd, a polyester, or a polyester amide.

43. A cosmetic composition according to claim 42, wherein the polymer in said aqueous polymer dispersion is an acrylic polymer.

44. A cosmetic composition according to claim 43, wherein said acrylic polymer is a copolymer of methyl methacrylate or styrene, with at least one monomer, wherein said at least one monomer is methyl acrylate, ethyl acrylate, 2-ethylhexyl acrylate, methyl methacrylate, ethyl methacrylate, or 2-ethylhexyl methacrylate.

45. A cosmetic composition according to claim 40, wherein the polymer in said aqueous polymer dispersion has a glass transition temperature of above or equal to 10° C.

46. A nail varnish comprising:
    a) at least one neutralized ionic film-forming polymer;
    b) water; and
    c) at least one polar organic solvent which is at least partially water-miscible and of higher boiling point than the boiling point of water;
    wherein the film-forming polymer is insoluble in water and is soluble in the organic solvent when it is in a non-neutralized state,
    wherein said neutralized film-forming polymer is soluble in the mixture of organic solvent and water, and
    wherein the mixture of neutralized polymer, organic solvent and water comprises a single phase, said single phase being a homogenous solution.

47. A nail care composition comprising:
    a) at least one neutralized ionic film-forming polymer;
    b) water; and
    c) at least one polar organic solvent which is at least partially water-miscible and of higher boiling point than the boiling point of water;
    wherein the film-forming polymer is insoluble in water and is soluble in the organic solvent when it is in a non-neutralized state,
    wherein said neutralized film-forming polymer is soluble in the mixture of organic solvent and water, and
    wherein the mixture of neutralized polymer, organic solvent and water comprises a single phase, said single phase being a homogenous solution.

* * * * *